United States Patent
Morra

(10) Patent No.: US 11,253,563 B2
(45) Date of Patent: Feb. 22, 2022

(54) COMPOSITION FOR USE IN THE TREATMENT AND/OR PREVENTION OF INFERTILITY

(71) Applicant: SERELYS PHARMA S.A.M., Monaco (MC)

(72) Inventor: Sossio Morra, Monaco (MC)

(73) Assignee: SERELYS PHARMA S.A.M., Monaco (MC)

(*) Notice: Subject to any disclaimer, the term of this patent is extended or adjusted under 35 U.S.C. 154(b) by 7 days.

(21) Appl. No.: 16/642,405

(22) PCT Filed: Aug. 27, 2018

(86) PCT No.: PCT/EP2018/073018
§ 371 (c)(1),
(2) Date: Feb. 27, 2020

(87) PCT Pub. No.: WO2019/042934
PCT Pub. Date: Mar. 7, 2019

(65) Prior Publication Data
US 2020/0197459 A1    Jun. 25, 2020

(30) Foreign Application Priority Data

Aug. 28, 2017 (FR) .................................. 1770894

(51) Int. Cl.

| | | |
|---|---|---|
| *A61K 36/15* | (2006.01) |
| *A61P 15/08* | (2006.01) |
| *A61K 9/00* | (2006.01) |
| *A61K 31/01* | (2006.01) |
| *A61K 31/122* | (2006.01) |
| *A61K 31/197* | (2006.01) |
| *A61K 31/355* | (2006.01) |
| *A61K 31/375* | (2006.01) |
| *A61K 31/4415* | (2006.01) |
| *A61K 31/525* | (2006.01) |
| *A61K 31/593* | (2006.01) |
| *A61K 31/714* | (2006.01) |
| *A61K 33/04* | (2006.01) |
| *A61K 33/30* | (2006.01) |
| *A61K 36/31* | (2006.01) |
| *A61K 36/899* | (2006.01) |

(52) U.S. Cl.
CPC ............ *A61K 36/15* (2013.01); *A61K 9/0053* (2013.01); *A61K 31/01* (2013.01); *A61K 31/122* (2013.01); *A61K 31/197* (2013.01); *A61K 31/355* (2013.01); *A61K 31/375* (2013.01); *A61K 31/4415* (2013.01); *A61K 31/525* (2013.01); *A61K 31/593* (2013.01); *A61K 31/714* (2013.01); *A61K 33/04* (2013.01); *A61K 33/30* (2013.01); *A61K 36/31* (2013.01); *A61K 36/899* (2013.01); *A61P 15/08* (2018.01)

(58) Field of Classification Search
None
See application file for complete search history.

(56) References Cited

FOREIGN PATENT DOCUMENTS

| | | |
|---|---|---|
| EP | 2135621 A1 | 12/2009 |
| FR | 2964834 A1 | 3/2012 |
| WO | 2002/017944 A1 | 3/2002 |

OTHER PUBLICATIONS

Liu et al. (CN106036878A Machine English Translation) (Year: 2016).*
"Graminex Flower Pollen Extract and its Effects on Fertility", Oct. 25, 2009, pp. 1-9.
Afsaneh Khademi et al., "The effect of L-carnitine on sperm parameters in patients candidated for Intracytoplasmic Sperm Injection", Iranian Journal of Reproductive Medicine, vol. 2, No. 2, Jan. 1, 2004, pp. 65-69.
Ann-Cathrin Hellstrom MD et al., "The pollen extract Femal—a nonestrogenic alternative to hormone therapy in women with menopausal symptoms", Menopause, vol. 19, No. 7, Jul. 1, 2012, pp. 825-829.
Maida Taylor MD, "Complementary and Alternative approaches to Menopause", Jan. 1, 2015, Elsevier.
K Winther et al., "Femal, a herbal remedy made from pollen extracts, reduces hot flushes and improves quality of life in menopausal women: a randomized, placebo-controlled, parallel study", Climacteric, vol. 8, No. 2, Jun. 3, 2005, pp. 162-170.
Piotr Czuczwar et al., "The safety and tolerance of Phytotherapies in menopausal medicine—a review of the literature", Przeglad Menopauzalny—Menopause Review, vol. 16, No. 1, Apr. 26, 2017, pp. 8-11.
WO, International Search Report with Written Opinion: PCT/EP2018/073018, dated Oct. 23, 2018 (21 pages).
WO, English Translation of International Search Report; PCT/EP2018/073018, dated Oct. 23, 2018 (5 pages).

\* cited by examiner

*Primary Examiner* — Quanglong N Truong
(74) *Attorney, Agent, or Firm* — FisherBroyles, LLP; Susan M. Oiler

(57) ABSTRACT

Compositions for treatment and/or prevention of infertility include a pollen extract and/or a pistil extract primarily obtained from plants belonging to the Pinaceae and/or Poaceae family.

11 Claims, No Drawings

COMPOSITION FOR USE IN THE TREATMENT AND/OR PREVENTION OF INFERTILITY

CROSS-REFERENCE TO RELATED APPLICATIONS

The present invention is filed under 35 U.S.C. § 371 as the U.S. national phase of International Patent Application No. PCT/EP2018/073018, filed Aug. 27, 2018, which designated the United States and which claims the benefit of French Patent Application No. 1770894, filed Aug. 28, 2017, which is hereby incorporated in its entirety including all tables, figures, and claims.

This invention relates to a composition based on plant extracts for use in the treatment and/or prevention of infertility.

Infertility can be thought of as a couple's inability to conceive after about a year of regular unprotected sex, or a woman's inability to carry a pregnancy to term. It also refers to sterility.

On average, more than one in ten couples consult a doctor for fertility problems. A male aetiology is found in nearly 40% of cases.

Normal male fertility is generally associated with the following conditions:
  a normal production of spermatozoa by the testicles (spermatogenesis), both in quality and quantity;
  good circulation of sperm within the male genitalia, which implies the absence of obstacles in the epididymides, vas deferens and urethra; and
  an adequate ejaculation.

Any factor that can hamper one of these mechanisms may be responsible for hypofertility, or even infertility (sterility), in men.

Semen analysis is the most important test in evaluating male fertility. The basic spermogram, or spermocytogram, accurately measures parameters such as semen volume, pH, the presence of leukocytes in the semen, sperm count, sperm motility in the first half hour, sperm morphology, and sperm vitality.

The results of the spermogram may vary depending on stress, the duration of abstinence, the consumption of alcohol, medication or drugs.

In order to judge the quality of the semen, certain data from the ejaculate are taken into consideration (World Health Organisation standards), including, but not restricted to:
  i. the volume of semen (normal volume between 1.5 ml and 6 ml):
    if the volume is equal to 0 ml, it is called aspermia;
    if the volume is greater than 6 ml, it is called hyperspermia;
    if the volume is less than 1.5 ml, it is called hypospermia.
  ii. The pH of the semen, which must be between 7.2 and 8.
  iii. Sperm concentration (normal concentration between 15 million and 200 million per ml of semen):
    if the concentration is over 200 million/ml, it is called polyspermia;
    if the concentration is less than 15 million/ml, it is called oligospermia;
    if the concentration is less than 5 million/ml, it is called severe oligospermia;
    if the concentration is less than 1 million/ml, it is more specifically referred to as cryptozoospermia; and
    the total absence of sperm in the ejaculate is called azoospermia.

In patients with sperm concentration problems, a distinction is usually made between patients with oligospermia and those with cryptozoospermia or azoospermia.

In fact, direct microscopic examination of a drop of semen does not reveal the presence of spermatozoa in the case of cryptozoospermia or azoospermia, unlike in the event of oligospermia, even in severe cases.

It is then necessary to carry out a thorough investigation by centrifugation of the semen and by examining the centrifugation pellet. When a few spermatozoa are found (less than 1 million spermatozoa per ml), it is called cryptozoospermia. The total absence of spermatozoa in the ejaculate, however, indicates azoospermia.

In addition, two distinct forms of azoospermia can be distinguished:
  "excretory" or "obstructive" azoospermia occurs when sperm are properly produced in the testicles, but there is a problem at any level of sperm transport in the male reproductive tract (epididymides, vas deferens, ejaculatory ducts) such that the sperm do not reach the ejaculate; and
  "secretory" or "non-obstructive" azoospermia occurs when there is no sperm produced by the testicles.
  iv. Total sperm motility can be classified as:
    progressive: when the spermatozoa are actively moving regardless of the speed;
    non-progressive: when the spermatozoa move but not forward; and
    immotile: when there is no movement.

A spermogram is considered normal if total motility (progressive and non-progressive) is greater than 40%.

This sperm motility is another parameter to be considered in preventing or treating male infertility. In fact, as soon as asthenospermia, i.e. low sperm motility (more than 65% are immotile) is added to oligospermia, the fertilising power becomes very low and tends towards zero for counts of less than 10 million/ml.
  v. Sperm morphology is also taken into consideration:
    if the morphology of normal sperm forms is less than 4% (Kruger), it is called teratospermia.

Therefore, male infertility is often due to an insufficient number of spermatozoa, a lack of motility or a high level of abnormal spermatozoa, a pH defect, abnormal volume of semen, lack of sperm vitality and/or abnormal leukocyte count (normal concentration below 1 million/ml), which may be combined, as is the case in oligoasthenospermic men.

There are also other factors associated with male infertility that may be the result of abnormalities in sperm penetration that are linked to antibodies, and in the level of concentrations of certain elements in the semen such as zinc, alpha-glucosidase and fructose.

At the molecular level, infertility may be associated with the disruption of certain signal transduction pathways, excessive production of Reactive Oxygen Species (ROS) or excessive activity of enzymes such as creatine phosphokinase. Infertility can also be investigated at the DNA level.

Secretory azoospermia has for many years been considered as a cause of permanent sterility, necessarily requiring the couple to turn to sperm donation, or to adopt.

Similarly, insufficient sperm in the semen of cryptozoospermic men can lead to a lack of natural fertility and require the couple to use a sperm donation or to adopt.

Nevertheless, before turning to sperm donation or adoption, most couples concerned first resort to new in vitro fertilisation techniques that consist of puncturing the testicles or epididymides in order to collect the sperm found there. These include ICSI (Intra Cytoplasmic Sperm Injection), with which, in theory, only a few sperm ejaculated or taken from the epididymis or testicle are needed, regardless of sperm concentration and motility, to achieve fertilisation and pregnancy, or IMSI (Intracytoplasmic Morphological Sperm Injection), which allows a very thorough selection of the best sperm in the ejaculate and significantly increases the chances of achieving fertilisation and therefore a child.

However, this fertilising power is never completely non-existent, and any couple can have natural pregnancies in spite of severe oligoasthenospermia.

Male infertility can, in some cases, be treated using surgical or medical techniques, but unfortunately the results are often disappointing. For this reason, specialists are increasingly turning to assisted reproductive technologies (ART), which sometimes provide more satisfactory results.

In practice, however, there is no question of waiting for this rare eventuality, and it is important to try to improve the quality of the sperm to increase the chances of natural fertilisation, thus avoiding the use of very expensive in vitro fertilisation techniques that consist of puncturing the testicles or epididymides in order to collect the spermatozoa found there, such as ICSI or IMSI, or the use of sperm donation or adoption.

Many studies on the causes of infertility and their treatment have already been carried out.

For example, it is known from the publication "Effect of Palm Pollen on Sperm Parameters of Infertile Man" (Athar Rasekh et al., Pakistan Journal of Biological Sciences 18 (4): 196-199, 2015) that the consumption of palm pollen (DPP for Phoenix dactylifera Date Palm Pollen) improves sperm count and motility.

The publication "Effects of pollen extract EA-10, P5 on chronic prostatitis or infertility with chronic prostatitis" (Acta Pharmacol Sin. 2002 Nov.; 23 (11): 1035-9, Chen et al.) also describes the effects of EA-10, P5 pollen oily and aqueous extracts on chronic prostatitis and on infertility related to chronic prostatitis. However, this publication recommends combining pollen extracts with an antibiotic such as roxithromycin to improve chronic prostatitis and related infertility.

The publication "Graminex Flower Pollen Extract and its Effect on Fertility" brings together various publications that disclose, among other things, that the pollen extract EA-10, P5 has been used in the treatment of infertility associated with chronic prostatitis.

The publication "Effects of pollen extract preparation PROSTAT/POLTIT on lower urinary tract symptoms in patients with chronic nonbacterial prostatitis/chronic pelvic pain syndrome: a randomized, double-blind, placebo-controlled Study ", (Urology 67 (1), 2006, James Elist) also indicates that the product PROSTAT/POLTIT, also comprising oily and aqueous extracts of pollen EA-10, P5 (74 mg pollen extract from Graminae species), effectively combats sexual dysfunction (libido, erection, ejaculation problems, etc.)

The product PROSTAL™ from MotiMa Laboratories contains purified, water-soluble and fat-soluble extracts of different pollen types such as P5 pollen and EA-10 pollen extracts. PROSTAL™ is known to date as a natural adjuvant for dealing with urinary discomfort and general tonus, a factor in sexual performance.

The publication by Khademi et al, 2004, discloses that treatment with L-carnitine improves sperm quality in men.

Application FR2964834 discloses a composition comprising vitamins B6, B9, B12, C, E, zinc, carnitine, coenzyme Q10 and lycopene for treating infertility and providing sperm protection.

Furthermore, application EP2135621 discloses a composition for treating male infertility comprising arginine, vitamins A, C, E, B6, B9, B12, coenzyme Q10, L-carnitine, zinc and selenium.

However, none of the above documents demonstrate or suggest any potentiated effect of a combination of several pollens and/or pistils, primarily obtained from plants belonging to the Pinaceae and/or Poaceae family, on an increase of sperm production and/or sperm motility in hypofertile or infertile men, especially in men with oligoasthenospermia, which is a specific patient group. On the other hand, none of the above documents suggest that the association of several pollens and/or pistils primarily obtained from plants belonging to the Pinaceae and/or Poaceae family can have a positive effect on spermogram parameters such as volume, pH, count, motility, concentration, morphology, vitality, and/or the presence of leukocytes, etc.

Finally, none of the above documents suggest that the combination of several pollens and/or pistils primarily obtained from plants belonging to the Pinaceae and/or Poaceae family can have a positive effect on sperm penetration, or at the level of concentrations of certain elements in the semen such as zinc, alpha glucosidase and fructose, or at the molecular level, involving certain signal transduction pathways, or by involving enzymes such as creatine phosphokinase, or at the DNA level.

In view of the above, one solution which the present invention proposes is to implement a composition capable of improving the production and/or quality of spermatozoa by the testicles in men, so as to improve their fertility, and thus avoid their having to turn to in vitro fertilisation, sperm donation or adoption in order to have a child.

Thus, the Applicant unexpectedly discovered that a composition comprising pollens and/or pistils primarily obtained from plants belonging to the Pinaceae and/or Poaceae family was able to increase sperm production in oligospermic men and sperm vitality and/or motility in asthenospermic men. Such a composition taken alone and, advantageously, in association with a plurality of other active ingredients acting in synergy, presents a remarkable potentiated activity, particularly on the motility, vitality and production of spermatozoa.

This invention's solution to the technical problem posed has the primary objective of creating a composition comprising a pollen extract and/or a pistil extract, with said pollen and/or pistil being obtained from plants belonging to the Pinaceae and/or Poaceae family, for its use in the treatment and/or prevention of infertility. More specifically, it's primary objective is a composition comprising a pollen extract and a pistil extract, said pollen and pistil being obtained from plants belonging to the Pinaceae and/or Poaceae family, for use in the treatment and/or prevention of infertility, in men with oligospermia, cryptozoospermia, azoospermia, asthenospermia, oligoasthenospermia and/or teratospermia. Preferably, the pathology to be treated is asthenospermia and/or teratospermia.

It also includes a method for preparing an aqueous pollen and pistil extract from plant(s) that preferably belong to the Pinaceae and/or Poaceae family, comprising the following steps:

a) aqueous extraction of pollen;
b) aqueous extraction of pollen and pistil;

c) spray-drying of the extracts obtained in steps (a) and (b);
d) recovery of said plant pollen and pistil extracts obtained in (c); characterised in that the extraction temperature is strictly below 45° C.

The invention further concerns an aqueous pollen and pistil extract, which can be obtained by the invention method, and its use in the treatment and/or prevention of infertility.

The invention and the benefits deriving from it will be better understood by reading the following description and non-limiting embodiments.

In this description, unless otherwise specified, it is understood that a given interval includes the upper and lower limits of that interval.

The invention relates to a composition used in the treatment and/or prevention of infertility comprising a pollen extract and/or a pistil extract, with the aforementioned pollen and/or pistil being obtained from plants belonging to the Pinaceae and/or Poaceae family.

"Treatment" means an improvement, prophylaxis or reversal of a disease or disorder, or of at least one discernible symptom thereof. It is also an improvement, prophylaxis or reversal of at least one measurable physical parameter related to the disease or disorder being treated that is not necessarily perceivable by the subject. In another way, the term "treatment" refers to the inhibition or slowing of the progression of a disease or disorder, either physically, such as stabilising a discernible symptom, physiologically, such as stabilising a physical parameter, or both. The term "treatment" also refers to delaying the onset of a disease or disorder. In certain individual embodiments of the invention, the composition of interest is administered as a preventive measure. In this context, the term "prevention" refers to a reduction in the risk of acquiring a specified disease or disorder.

According to the invention, we speak of extraction when we use a solvent, advantageously environmentally-friendly when water, glycerin, glycols, ethers, oils, hydroalcoholic mixtures, ethanol and other alcohols are used, on a vegetable raw material to extract certain compounds or molecules from it, after possible mixing, decanting and filtration.

The solvent can then be partially or completely removed to obtain an extract.

After collection, the pollen can be used fresh or dried, preferably dried, and possibly sterilised.

The pollen and/or pistil extracts described herein may be oily and/or aqueous extracts.

Oily extract means an extract containing fat-soluble active ingredients obtained by extraction, for example maceration, infusion, digestion, decoction, percolation or leaching, with maceration the preference at room temperature between 15 and 27° C., of a vegetable raw material in an oily solvent such as an ether, ketone or oil.

As non-limiting examples, the oily solvent is an ether such as diethyl ether or a ketone such as acetone.

The inventive composition preferably comprises an aqueous pollen and/or pistil extract, and more preferably an aqueous pollen extract and an aqueous pistil extract.

Aqueous extract means an extract containing water-soluble active ingredients obtained by extraction, for example hydrodistillation, maceration, infusion, digestion, decoction, percolation or leaching, preferably maceration at low temperatures between 15 and 40° C., of a vegetable raw material in an aqueous solvent, i.e. a solvent comprising water taken alone or advantageously mixed with other solvent(s) such as an alcohol, a ketone, and/or a non-ionic surfactant.

As non-limiting examples, the aqueous solvent is selected from a mixture comprising primarily of water combined with an alcohol such as ethanol, a ketone such as acetone, and/or a non-ionic surfactant.

The pollen and/or pistil extracts used in the inventive composition are obtained from plant(s) of the Poaceae and/or Pinaceae family.

Poaceae, also known as grasses (Gramineae), are a family of monocotyledonous plants within the poale order. This family, consisting of about 12,000 species in 780 genera, includes most of the species commonly known as "grasses" and "cereals". They are generally herbaceous plants and are less frequently ligneous (bamboos).

Like all anemophilic pollens, Poaceae pollen is spherical or slightly ellipsoidal in shape with reduced ornamentation. The single aperture (or pore) is round: this is one of the criteria for monocotyledons. Poaceae pollen is small and light. Its size is around 40 microns. For cereals, the size is in the range of 60 to 100 microns.

The pine family (Pinaceae) includes gymnosperms; it has 220-250 species divided into 11 genera. They are trees or shrubs, from temperate regions, that either evergreen, with needles or scales, or deciduous like larch trees. In this family, species native to France are found in the genera *Abies* (firs), *Picea* (spruces), *Larix* (larches), and *Pinus* (pines).

Pinaceae produce large pollen grains in abundance, usually between 40 and 100 microns in size, and are poreless. The pollen grains of pine, fir, spruce and cedar have two balloons that facilitate their suspension in the air. The pollen grains of larches and Douglas firs are more or less spherical and without balloons.

Preferably, the plants from which the pollen and/or pistil are obtained are selected from the genera *Secale, Zea, Pinus* and/or *Dactylis*, or a mixture thereof.

In particular, the plants from which the pollen and/or pistil are obtained are preferably selected from *Secale cereale* L. (rye), *Zea mays* L. (maize), *Pinus sylvestris* L. (Scots pine), and/or *Dactylis glomerata* L. (cocksfoot), or a mixture thereof.

Preferably, the plants from which the pollen and/or pistil are obtained are freshly harvested. The pollens used for this invention may be harvested by insects (such as bee pollen) or harvested by human intervention. Bee pollen, for example, contains pollen, but also nectar and bee saliva. Pollen collected through human intervention is free of such additional ingredients. Preferably, said pollen for these compositions is only obtained by human intervention. This further allows for the final product to be standardised.

The compositions used according to the present invention are advantageously rich in superoxide dismutase (SOD), tannins, polyphenols, vitamins, enzymes and trace elements, amino acids, fatty acids, and minerals. Furthermore, the compositions used according to the present invention do not contain hormones, such as phytoestrogens.

Advantageously, pollen extracts are obtained from the cytoplasm (inner part of the pollen seed without its shell). As the shell is generally a source of allergens, and an obstacle to the availability of cytoplasmic compounds, the use of a cytoplasmic pollen extract has a clear advantage over the use of a natural pollen extract. Such purified cytoplasmic extracts of specific, standardised pollen also have a high content of superoxide dismutase (SOD), tannins, polyphenols, vitamins, enzymes and trace elements, amino acids, fatty acids and minerals, as well as beneficial proteins and carbohydrates. The concentration of beneficial compounds in the different extracts is much higher than the amount of valuable compounds in raw pollen.

It has been shown that a composition comprising specific, standardised, purified cytoplasmic pollen extracts of a mixture of plant material from several plants is more effective on infertility in comparison with compositions comprising extracts from only one plant.

Particularly advantageously, the inventive composition includes:
a pollen extract from *Secale cereale* L.;
a pollen extract from *Zea mays* L.;
a pollen extract from *Pinus sylvestris* L.;
a pollen extract from *Dactylis glomerata* L.; and
a pistil extract from *Zea mays* L.

Even more advantageously, the inventive composition includes:
an aqueous pollen extract from *Secale cereale* L.;
an aqueous pollen extract from *Zea mays* L.;
an aqueous pollen extract from *Pinus sylvestris* L.;
an aqueous pollen extract from *Dactylis glomerata* L.; and
an aqueous pistil extract from *Zea mays* L.

Preferably, the inventive composition comprises:
45% to 90% aqueous pollen extract from *Secale cereale* L. by weight based on the total weight of the extract;
1% to 35% aqueous pollen extract from *Zea mays* L. pollen by weight based on the total weight of the extract;
0.01% to 5% aqueous pollen extract from *Pinus sylvestris* L. by weight based on the total weight of the extract;
3% to 30% aqueous pollen extract from *Dactylis glomerata* L. by weight based on the total weight of the extract; and
0.1% to 10% aqueous pistil extract from *Zea mays* L. by weight based on the total weight of the extract.

Preferably, the daily dose of the aqueous pollen and/or pistil extracts of the inventive composition is between 160 mg and 480 mg, and more preferably between 160 and 320 mg. This daily dose is preferably administered in 1, 2 or 3 doses (morning, noon and/or evening), for example by way of 1, 2, 3, 4 or 6 tablets.

The final weight of the tablet is preferably between 300 mg and 1000 mg. Even more preferably is between 325 and 650 mg.

Particularly advantageously, the final weight of the tablet is 650 mg.

The composition used according to the invention is advantageously administered for a period of at least three months, preferably six months, i.e. more than two cycles of sperm production. Advantageously, such a lengthy treatment period will make it possible to try to generate the production of sufficient spermatozoa with good motility and quality (volume, pH, count, morphology, vitality, etc.) through the testicles in men producing few fertile sperm, so that they can regain natural fertility or at least significantly increase the chances of finding fertile sperm in the ejaculate for in vitro fertilisation, and thus avoid having to turn to sperm donation or adoption in order to have a child.

The inventive composition is advantageous in improving sexual desire (libido), erectile dysfunction or ejaculation. Improving these disorders also increases the likelihood of having a child.

Another purpose of this invention concerns a food supplement comprising the composition used according to the invention.

Pollen or pollen preparations are generally consumed as a dietary supplement. They can be taken in their rudimentary form, which are pollens in their own right, or as a powder in free or encapsulated form.

The composition used according to the invention also comprises a physiologically acceptable medium proportionate to a reasonable benefit/risk ratio, comprising known excipients commonly used in phytotherapy such as binding agents, disintegrating agents, bulking agents, dispersing agents, agglomerating agents, lubricants, wetting agents, surfactants, emulsifiers, thickeners, slip agents, flavouring agents, sweetening agents, colourants, coating agents, stabilisers and/or preservatives.

The person skilled in the art shall take care to choose these possible excipients and their quantity in such a way that they do not impair the desired properties of the compositions used according to the invention.

Examples of excipients include cellulose, preferably microcrystalline cellulose, and silicon dioxide.

Preferably, the inventive composition also includes coenzyme Q10.

In fact, coenzyme Q10 reduces oxidative stress in the seminal fluid and increases antioxidant enzyme activity. The publication "*Effect of Coenzyme Q10 supplementation on antioxidant enzyme activity and oxidative stress of seminal plasma: a double-blind randomised clinical trial.*" (Andrologia. 2013 Jan. 7. doi: 10.1111/and.12062, Nadjarzadeh et al.) indicates that coenzyme Q10 supplementation in infertile men reduces oxidative stress in seminal fluid, improves sperm quality and increases antioxidant enzyme activity.

Advantageously, the inventive composition further comprises at least one amino acid, a carotenoid, a trace element, an inositol stereoisomer and/or a vitamin and/or a root extract, taken alone or as mixtures. Preferably:
the amino acid is lysine, methionine or carnitine, preferably L-carnitine;
the carotenoid is lycopene;
the trace element is selected from zinc and selenium;
the inositol stereoisomer is myo-inositol;
the vitamin is selected from vitamin B6, vitamin B9, vitamin B12, vitamin C, vitamin D and vitamin E; and
the root extract is a maca root extract (*Lepidium meyenii*).

This plurality of ingredients that are specifically chosen and combined according to the invention allows correlations between these active ingredients which act in synergy in the composition used according to the invention to generate and especially to optimise the production and motility of spermatozoa in hypofertile or infertile men, and to generally improve the quality, and more particularly the vitality, of the spermatozoa thus produced (in particular the pH, count, morphology, vitality, etc.).

The inventive composition can be administered orally in one or more identical or different formulations. It is provided in any dosage form normally used for oral administration and particularly in the form of a pill, tablet, capsule, soft capsule, sugar-coated pill, sachet, tube, bottle, chewing gum, ball, emulsion, suspension, liquid, solution, vial, drink, syrup, powder, solid, soft gel, or semi-solid.

Advantageously, the composition is formulated as a tablet, capsule, soft gel, semi-solid, solid, liquid or powder.

Particularly advantageously, the composition for its use according to the invention is administered once a day and is in the form of a tablet, preferably 650 mg in weight.

In general, the inventive compositions can be obtained by mixing different pollen and/or pistil extracts that have been obtained separately by different extraction processes, which may be identical or different. Thus, the inventive composition may, for example, comprise a first pollen and pistil extract combined with a second pollen extract. Advantageously, the first pollen and pistil extract is a combined extract of purified pollen and pistil cytoplasm, containing a high potency of an antioxidant enzyme, superoxide dismutase (SOD). The second pollen extract is a purified cytoplasmic pure pollen extract. Pollen and pistils are selected and harvested, separately and in a standardised manner, from members of the Poaceae family. Cultivation and harvesting of the defined species shall be carried out in separate fields under a quality control duly established in accordance with Good Agricultural and Collection Practices for medicinal plants. Pollen is selected for the preparation of the second pollen extract, while the selected pollen and pistils are mixed in a standardised manner to produce the formulation of the first extract. During the extraction process, carried out in accordance with Good Manufacturing Practices, pollen and pistils are treated with enzymes to enable germinal opening. The extract is then recovered by filtration, leaving pollen grain shells aside, which can be allergenic. The extract is defined by high-performance liquid chromatography (HPLC) and gas chromatography (GC) to guarantee the quantity of active ingredients. The extract is mixed in a standardised formula. This standardisation procedure results, for example, in tablets containing 100-140 mg of the first pollen and pistil extract and 20-60 mg of the second pollen extract.

Advantageously, the Applicant has developed an alternative process for the simultaneous production of a pollen and/or pistil extract by successive aqueous extractions.

Controlling the manufacturing parameters makes it possible to homogenise and preserve the quality of the pollen and/or pistil extracts of the species used, in particular, by preventing the denaturation of certain proteins.

Thus, the inventive process makes it possible to ensure that the species in the pollen and/or pistil extract can be traced.

In addition, the titre of the pollen and/or pistil extract is standardised in amino acids at its final stage of manufacture. By this control of the manufacturing parameters, traceability and standardisation of the amino acid titre are ensured, allowing excellent intra-batch reproducibility framed by an extract specification.

The invention therefore has a second aim of a process for preparing an extract of pollen and pistil of plant(s), preferably belonging to the Pinaceae and/or Poaceae family, comprising the successive steps of:
a) aqueous extraction of pollen;
b) aqueous extraction of pollen and pistil;
c) spray-drying of the extracts obtained in steps (a) and (b);
d) recovery of said plant pollen and pistil extracts obtained in (c).

The Applicant was able to demonstrate that the extraction stage was particularly delicate. Thus, the extraction temperature must be strictly below 45° C. Above this temperature, one or more of the pollens and pistils detailed above are no longer present (absence of specific markers). The quality of the composition and/or its efficacy are not, therefore, assured.

The extraction temperature should preferably be below 42° C.

The duration of the extraction stage, for each of the extracts, is preferably at least 6 hours, more so at least 10 hours, and even more preferably at least 12 hours.

In addition, the Applicant was able to demonstrate that separation under overly prolonged conditions degraded the extracts. Thus, when the extraction is coupled with a separation, it must not exceed 6000 revolutions per minute (rpm), preferably 4500 rpm, and even more preferably 2800 rpm.

The process thus developed guarantees good traceability of the pollens and pistils used. Indeed, the Claimant was able to show that the extracts manufactured according to the prior art processes do not make it possible to find the presence of one or more markers of pollens and pistils and thus, de facto, the presence of all the pollen and/or pistil extracts in the composition.

The prior art compositions are therefore not homogeneous and do not contain, in the final composition, all the expected pollen and/or pistil extracts.

The process, which is the object of the invention, advantageously comprises additional separation, filtration and/or evaporation steps, making it possible to increase the concentration of the final extract or to optimise the preparation of said extract.

The inventive process also possesses the following advantages:
it allows for standardisation;
it has excellent reproducibility;
it allows for reduced costs by optimising and limiting the number of industrial resource operations.

It also makes it possible to trace the presence of extracts in the inventive composition and thus ensure its quality and thereby its effectiveness.

Advantages that reduce handling and costs include:
simplified planning;
use of optimised equipment;
reduced non-productive time (cleaning, batch change, number of validations, etc.);
limited management of reference numbers;
a reduction in risky operations (cleaning, weighing, work procedures, reduced costs in validation, stability, simplified tablet formulation, microbiological risk, traceability, etc.).

Taking into account the fact that the inventive preparation method makes it possible to obtain an extract of pollen and pistil containing markers which cannot be identified when using the prior art extract preparation method, the invention also has the aim of obtaining an extract of pollen and pistil, preferably belonging to the Pinaceae and/or Poaceae family, which can be obtained according to the preparation method described above.

Preferably, it is an aqueous pollen and/or pistil extract of *Secale cereale* L., *Zea mays* L., *Pinus sylvestris* L. and/or *Dactylis glomerata* L., obtainable by the preparation process comprising the following steps of:
a) extraction with water of *Secale cereale* L., *Zea mays* L., *Pinus sylvestris* L. and/or *Dactylis glomerata* L. pollens at a temperature below 45° C. in order to obtain a first extract;
b) extraction with water of *Zea mays* L. pollens and pistils at a temperature below 45° C. in order to obtain a second extract;
c) mixture of the first and second extracts obtained in (a) and (b);
d) spray-drying of the mixture obtained in (c);
e) recovery of the pollen and pistil extract mixture obtained in (d).

The extraction temperature for each of the extracts should preferably be below 42° C.

It is even more preferable for an aqueous extract of *Secale cereale* L., *Zea mays* L., *Pinus sylvestris* L. and/or *Dactylis glomerata* L. pollen and/or pistil, as described above, to be used in infertility treatment and/or prevention.

The Applicant was able to demonstrate that the production of a composition from plant extracts often requires specific production steps, such as spray-drying and granulation.

These steps can have an impact on the final composition and its constituents, including proteins. Certain proteins that are present in the raw vegetable material are likely, due to the specific nature of the manufacturing process (typically spray-drying), to lose their potency or be lost. In particular, the Applicant was able to demonstrate that the use of an optimised spray-drying process (temperature difference of 50° C. between inlet and outlet temperature) avoided the denaturation of the target proteins concerned. The Applicant also found that the presence in the final composition of at least one of these proteins or peptides derived from these target proteins ensures the composition's quality. The extracts used in the composition are thus optimal and of pharmaceutical quality, given that the composition activity is not being altered. In addition, by providing adequate quality control, better content consistency can be ensured, which is important when treating patients for specific symptoms and/or discomforts.

In addition, the composition is highly reproducible between different batches (in terms of quality and ingredients present), allowing for quality control, standardisation, batch traceability, and reproducible protein profiling. It thus complies with good manufacturing practices for pharmaceutical products and food supplements on the market (pharmaceutical-grade botanical products). This reproducibility also ensures that each new batch of pollen extract and/or pistil extract meets the established specifications and therefore has the same physiological activity as the batches used in the clinical studies. The manufacturing process makes it possible to obtain the desired beneficial compound.

The present invention relates to oral compositions which comprise at least one component derived from pollen extract and/or pistil of plant(s) belonging to the Pinaceae and/or Poaceae family and in which the presence of one or more protein markers is detectable, wherein these protein markers are a good indication of the quality of the final composition. These markers can also be used for standardising compositions.

Said markers or tracers are advantageously proteins or peptides derived from proteins, with said proteins being selected from the group of reticuline oxidase, endochitinase A, beta-1,3-glucanase, exopolygalacturonase, non-specific lipid transfer protein or any combination thereof.

According to the invention, the presence of specific markers of proteins or peptides derived from these proteins (markers) can be confirmed in the final composition, said markers being indicative of the quality of the composition and which can therefore be used for standardisation and quality control.

Indeed, the Applicant was able to show that the presence of certain tracers or markers (protein or peptide derived from said protein) was capable of confirming the presence of certain pollen and/or pistil extracts in the final composition.

Thus, the Applicant was able to demonstrate that the following proteins or peptides derived from these proteins allow the following pollens and/or pistils to be traced:

pollen allergen Sec 4 (*Secale cereale*) (Q5TIW8 and Q5TIW7) and glucan endo-1,3-beta-D-glucosidase (Q1EM97), for example, allow the presence of the pollen *Secale cereale* L. to be traced;

reticulin oxidase (Reticulase Oxidase) (B6T5D7), beta-1,3-glucanase (E1AFV5), pectinesterase (B6UCK8), Extensin-like protein (Q9SPM0), exopolygalacturonase (PGLR2), beta-amylase (Q9SYS1) and chitinase (DOEM57), for example, allow the pistils and pollens of *Zea mays* L. to be traced;

pollen allergen Lol p4, for example, allows the presence of the pollen *Dactylis glomerata* L. to be traced; and lipid transfer protein makes it possible, for example, to trace the presence of *Pinus sylvestris* L. and/or *Zea mays* L. pollen.

Said proteins or peptides derived from said proteins that are present in the final extracts, and indeed in the composition used according to the invention, are preferably selected from the group of reticuline oxidase (Reticulase Oxidase), endochitinase A, beta-1,3-glucanase, exopolygalacturonase, non-specific lipid transfer protein or any combination of the foregoing.

The extracts of the composition, which is the object of the invention, advantageously comprises at least one second protein or a peptide derived from said second protein selected from the group consisting of the *Dactylis glomerata* L. pollen allergen Lol p4, of the pollen allergen Sec 4 (*Secale cereale*), glucan endo-1,3-beta-D-glucosidase, beta-amylase, chitinase, or any combination thereof.

The Applicant was able to demonstrate that the absence of one or more of these markers or tracers, specific to certain pollens and/or pistils, in the extracts containing the a priori aforementioned pollens and/or pistils and consequently in the compositions containing such a priori extracts were qualitative indicators of the products.

Thus, the absence of a specific marker of a given pollen and/or pistil indicates that the extract or composition does not comprise said pollen and/or pistil, or that they have been denatured, thereby rendering the composition comprising at least one such pollen and/or pistil extract degraded, ineffective or less effective at the very least.

Finally, the invention's final purpose is a composition or extract as described above, for use in the treatment and/or prevention of infertility, in particular for use in improving the quality of a patient's sperm. This improvement in semen quality is particularly evident in the following parameters:
semen volume;
the pH of the semen;
sperm concentration;
total sperm motility;
sperm density;
sperm vitality and morphology; or
the presence of leukocytes.

According to a particular embodiment of the invention, the product or composition are used in the treatment and/or prevention of infertility that is not associated with inflammation of microbacterial origin, such as prostatitis. Thus, no antibiotic is in combination with the inventive composition or product.

Indeed, male infertility, within the context of the invention, is understood to be infertility that is unrelated to the prostate.

This invention will now be illustrated with the following examples:

EXAMPLE 1

Inventive Compositions i. Composition A:
Dosage form: Tablet
Tablet weight: approx. 380 mg
Aqueous pollen extract: about 40% by weight based on the total weight of the composition

TABLE 1

Ingredients of the extract expressed by weight based on the total weight of the final pollen extract:

| Ingredients | Quantity % |
| --- | --- |
| Secale cereale L. Pollen | 70-80 |
| Zea mays L. Pollen | 15-40 |
| Dactylis glomerata L. Pollen | 5-10 |

Other ingredients in the final product, for example, include: microcrystalline cellulose, silicon dioxide, magnesium stearate and/or coating agents. Talc and shellac were used as a coating agent. The recommended daily dose is two tablets per day, to be taken in the morning or evening.

The pollen extract for the above tablet was obtained using a conventional process for the preparation of pollen and/or pistil extracts.

ii. Composition B:
Dosage form: Capsule
Tablet weight: approx. 380 mg or 640 mg
Aqueous pollen extract: about 40% by weight based on the total weight of the composition

TABLE 2

Ingredients of the extract expressed by weight based on the total weight of the final pollen and pistil extract:

| Ingredients | Quantity % |
| --- | --- |
| Zea mays L. Pollen | 15-80 |
| Pinus sylvestris L. Pollen | 0.05 to 25.00 |
| Zea mays L. Pistil | 1-15 |

Other ingredients in the final product, for example, include: microcrystalline cellulose, silicon dioxide, magnesium stearate and/or coating agents. Talc and shellac were used as a coating agent. The recommended daily dose is one or two tablets per day, to be taken in the morning or evening.

The pollen and pistil extract for the above tablet was obtained using a conventional process for the preparation of pollen and/or pistil extracts.

iii. Composition C:
Dosage form: Tablet
Tablet weight: approx. 380 mg or 640 mg
Aqueous pollen extract: about 40% by weight based on the total weight of the composition

TABLE 3

Ingredients of the extract expressed by weight based on the total weight of the final pollen and pistil extract:

| Ingredients | Quantity % |
| --- | --- |
| Secale cereale L. Pollen | 45-90 |
| Zea mays L. Pollen | 1-35 |
| Pinus sylvestris L. Pollen | 0.01 to 5.00 |
| Dactylis glomerata L. Pollen | 3-30 |
| Zea mays L. Pistil | 0.1-10 |

Other ingredients in the final product, for example, include: microcrystalline cellulose, silicon dioxide, magnesium stearate and/or coating agents. Talc and shellac were used as a coating agent. The recommended daily dose is two tablets per day, to be taken in the morning or evening.

The pollen and pistil extract for the above tablet was obtained using a conventional process for the preparation of pollen and/or pistil extracts.

iv. Composition D:
Dosage form: Tablet
Tablet weight: approx. 380 mg or 640 mg
Aqueous pollen extract: about 40% by weight based on the total weight of the composition

TABLE 4

Ingredients of the extract expressed by weight based on the total weight of the final pollen and pistil extract:

| Ingredients | Quantity % |
| --- | --- |
| Secale cereale L. Pollen | 45-90 |
| Zea mays L. Pollen | 1-35 |
| Pinus sylvestris L. Pollen | 0.01 to 5.00 |
| Dactylis glomerata L. Pollen | 3-30 |
| Zea mays L. Pistil | 0.1-10 |

Other ingredients in the final product, for example, include: microcrystalline cellulose, silicon dioxide, magnesium stearate and/or coating agents. Talc and shellac were used as a coating agent. The recommended daily dose is two tablets per day, to be taken in the morning or evening.

The pollen and pistil extract for the above tablet was obtained using the process, which is the object of the invention, detailed in Example 2 below.

v. Composition E:
Dosage form: Tablet
Tablet weight: approx. 650 mg
Aqueous pollen extract: about 40% by weight based on the total weight of the composition

TABLE 5

Ingredients of the extract expressed by weight based on the total weight of the final pollen and pistil extract:

| Ingredients | Quantity % |
| --- | --- |
| Secale cereale L. Pollen | 45-90 |
| Zea mays L. Pollen | 1-35 |
| Pinus sylvestris L. Pollen | 0.01 to 5.00 |
| Dactylis glomerata L. Pollen | 3-30 |
| Zea mays L. Pistil | 0.1-10 |

In addition, the final product contains approximately 2-10 mg of zinc and other ingredients such as microcrystalline cellulose, silicon dioxide, vitamin E, magnesium stearate and/or coating agents. Talc and shellac were used as a coating agent. The recommended daily dose is one tablet per day, to be taken in the morning or evening.

The pollen and pistil extract for the above tablet was obtained using the process, which is the object of the invention, detailed in Example 2 below.

The presence of reticuline oxidase, endochitinase A, beta-1,3-glucanase, exopolygalacturonase, and non-specific lipid transfer protein was confirmed with LC-MS/MS.

The compositions according to the invention are used in the treatment and/or prevention of infertility, particularly in men.

Preferably, the composition, which is the object of the invention, is intended for the treatment and/or prevention of infertility in men with oligospermia, cryptozoospermia, azoospermia, asthenospermia, oligoasthenospermia and/or teratospermia.

More preferably, the composition, which is the object of the invention, is intended for the treatment of infertility in men presenting, in particular, with oligoasthenospermia.

Even more preferably, the composition, which is the object of the invention, is intended for the treatment of infertility in men with asthenospermia and/or teratospermia.

EXAMPLE 2

Production of a Spray-Dried Extract According to an Aspect of the Present Invention The process for the preparation of the extract described here is an aqueous extraction, allowing a controlled selection of the water-soluble proteins of interest. The chronology of the operations and the control of the manufacturing parameters allow the preservation of specific proteins or peptides that are characteristic of the species used. This ensures that the species in the extract can be traced. The titre of the extract is advantageously standardised in amino acids at its last stage of manufacture, during nebulisation. By this control of the manufacturing parameters, the traceability, standardisation of the amino acid titre and intra-batch reproducibility, framed by an extract specification, are ensured.

i. Preparation of pollen and pistil extracts according to the innovative process:

The appropriate time for harvesting is:

June-July for rye pollen (*Secale cereale* L.) and cocksfoot pollen (*Dactylis glomerata* L.);

July-September for maize pollen and pistil (*Zea mays* L.);

May-June for Scots pine pollen (*Pinus sylvestris* L.).

Pine pollen is harvested from the wild, the other pistils and pollen come from agricultural crops.

Pollens and pistils are dried.

The process can be characterised by the following main steps:

a) aqueous extraction (preferably water and/or surfactant) of pollen;
b) aqueous extraction (preferably water and/or surfactant) of pollen and pistil;
c) spray-drying of the extracts obtained in steps (a) and (b) above; and
d) recovery of said plant pollen and pistil extracts obtained in (c).

Surprisingly, the Applicant was able to identify that, by modifying the operating conditions of the process for preparing the extracts intended for developing the inventive compositions, it was possible to increase the quality of the extracts.

ii. Details of the main steps of the preferred process according to the invention:
a. Extraction steps:
The Applicant was able to demonstrate that the temperature of the extractions should be between 30° C.-45° C.
Extraction is preferably carried out under continuous agitation for 12 to 90 hours.
b. Spray-drying step of the extract mixture:
The different extracts, preferably previously evaporated, filtered and/or decanted, are mixed to obtain a dry-substance content between 30% and 50%.
The starting temperature of the spray-drying stage is between 138° C. and 168° C.

EXAMPLE 3

Comparison of C and D Compositions from Two Different Processes

Composition D, obtained by the method described above (example 2), is compared with composition C, obtained by the prior art method, for which the extraction temperature is strictly above 45° C.

The Applicant noted that the change in extraction temperature and physical separation conditions affect the result of the identification tests.

The protein Q5TIW3 (marker of *Dactylis glomerata* L. pollen) is not present in the batches of extracts obtained by the prior art method, whereas it is present in the batches of extracts obtained by the method described in Example 2 above.

Species cannot be traced with the old process.

The development of the process is a response to a requirement for traceability and reproducibility while integrating industrial economic constraints. The search for markers/tracers in the extracts manufactured according to the prior art and those manufactured with the inventive process shows that the prior art processes do not make it possible to ensure that the species used can be tracked.

TABLE 6

Markers or tracers present in two compositions whose extracts are obtained by two different processes:

| Species | Extract markers from the process according to example 9 (T ° < 45° C.) | Extract markers from the process according to the prior art (T ° C. > 45°) |
|---|---|---|
| Pollens from *Secale cereale* L. | Q5TIW8 - pollen allergen Sec 4 | Q5TIW8 - pollen allergen Sec 4 |
| Pollens and pistils from *Zea Mays* L. | B6T5D7 - Reticulase oxidase<br>E1AFV5 - Beta-13-glucanase | B6T5D7 - Reticulase oxidase<br>E1AFV5 unidentified |
| Pollens from *Dactylis glomerata* L. | Q5TIW3 pollen allergen LoI p4 | Unidentified |
| Pollens from *Pinus sylvestris* L. | Lipid transfer protein, positive immunological response | Lipid transfer protein, positive immunological response |

EXAMPLE 4

Effectiveness of Inventive Compositions i. Tested compositions:
In this example, the effects of compositions whose pollen and pistil extracts are obtained by the inventive process (composition D above) have been compared with prior art compositions.
ii. Observational study process:
The aim of this study is to evaluate the impact of a six-month treatment with composition D or with other prior art compositions (substantially of the same dosage form, the same weight and the same concentration of pollen extract in the composition) including pollen extracts (EA10P5, EA5P2, etc.) on the main spermatic parameters (cf. see below) in a population of men in consultation for a fertility problem and who are more precisely presenting with oligospermia, asthenospermia or oligoasthenospermia.

We are focusing on analysing the impact of such a treatment, particularly in terms of sperm count and/or sperm motility in the patients included in the study.

Unless otherwise specified, at the start of treatment visit, the compositions are given to the patient for a six-month course of one dose per day. The recommended daily dose is two tablets per day, to be taken in the morning or evening. Intake starts the same day.

During the final visit of the trial, a post-treatment spermogram is performed. Treatment adherence is also assessed.

Surprisingly, it has been shown that three months of administration of composition D improves semen quality more than a prior art composition, especially with regard to general sperm motility.

In fact, it has been observed that motility is improved by at least 15%, whereas it is only improved by about 10% with a composition including EA10P5 pollen.

Similarly, it has been shown that composition D improves sperm vitality, whereas it is reduced by about 15% with a composition comprising EA10P5 pollen.

Furthermore, the Applicant observed that composition D, which is the object of the invention, also improves certain disorders such as sexual dysfunction, decreased libido, erectile dysfunction, and premature or delayed ejaculation.

The Applicant also compared the effects of composition D, which is the object of the invention, on semen parameters with another composition comprising palm pollen (*Phoenix dactylifera*). The Applicant was therefore able to show that composition D improves the number of spermatozoa per ml of semen by more than 60% after six months of treatment, whereas it is only improved by about 50% with an equivalent composition comprising palm pollen (*Phoenix dactylifera*).

Finally, the Applicant compared the different parameters of a spermogram of 25 patients before and after treatment with composition D for a period of six months.

The Applicant observed that the parameters of the spermogram were improved, including the following parameters:
Volume
pH
Count
Motility
Morphology
Vitality
Leukocytes All of these studies therefore highlight an unexpected potentiated effect in a patient population with the administration of inventive composition D, which significantly increases the chances of finding fertile spermatozoa in the ejaculate by enabling the generation of the output of motile spermatozoa in hypofertile or even infertile men presenting with both oligospermia and asthenospermia, and therefore producing no or substantially no fertile spermatozoa.

All patients evaluated in the study responding favourably to treatment with inventive composition D now produce a sufficient concentration of spermatozoa with adequate motility per ml of ejaculate to provide natural fertilisation, and thus avoid the situation whereby the patients must turn to sperm donation or adoption to have a child.

EXAMPLE 5

Spermogram Parameter Results Obtained after Treatment with Inventive Composition E on Infertile Patients During the first enrolment visit, patients undergo a spermogram before treatment. At the start of treatment, the product is given to them for a treatment of one daily intake for three months. The recommended daily dose is one tablet per day, to be taken in the morning or evening. Intake starts the same day. During the final visit of the trial, a post-treatment spermogram is performed. Treatment adherence is also assessed. The sampling conditions are strict. Semen collection is done by masturbation. Semen is collected after two to four days of sexual abstinence, after careful disinfection of the glans, and when the subject is not experiencing a period of fever.

Comparative results (before and after treatment) are detailed below:
i. Information about the patient(s) whose results are listed in Table 7 below:
   non-smoker
   grade 2/3 left varicocele (Varicocele is characterised by the dilation of a vein (varicose vein) in the spermatic cord, a fibrous cord located in the sacs above each testicle, which connects each one to the scrotum)
   no other treatment is taken
   no vitamin supplementation at the start of treatment

TABLE 7

| PARAMETERS | 2010 WHO Standards | Before treatment | After treatment |
| --- | --- | --- | --- |
| volume | >1.5 ml | >1.5 ml | >1.5 ml |
| pH | 7.2-8 | 7.2-8 | 7.2-8 |
| Count | 15 million/ml | 10 million/ml | no change |
| Motility | >40% total motility >32% progressive motility | 26% total motility | 35% total motility |
| Morphology | >4% according to Kruger | >4% according to Kruger | >4% according to Kruger |
| Vitality | >58% | >58% | >58% |
| leukocytes | <1 million/ml | <1 million/ml | <1 million/ml |

Conclusion on the results presented in Table 7:

Before treatment, sperm concentration is low (10 million/ml) and there is a hypo-motility of 26%. The other parameters are normal. After treatment, the sperm concentration remains unchanged, but the motility is increased to 35%. No adverse effects are reported.

ii. Information about the patient(s) whose results are listed in Table 8 below:
smoker, less than 20 packs a day;
no comorbidities;
no other treatment is taken;
no vitamin supplementation at the start of treatment.

TABLE 8

| PARAMETERS | 2010 WHO Standards | Before treatment | After treatment |
| --- | --- | --- | --- |
| volume | >1.5 ml | >1.5 ml | no change |
| pH | 7.2-8 | 7.2-8 | no change |
| Count | 15 million/ml | <1 million/ml | <1 million/ml |
| Motility | >40% total motility >32% progressive motility | >40% total motility >32% progressive motility | no change |
| Morphology | >4% according to Kruger | >4% according to Kruger | no change |
| Vitality | >58% | >58% | no change |
| leukocytes | <1 million/ml | <1 million/ml | no change |

Conclusion on the results presented in Table 8:

Before treatment, the patient experiences cryptozoospermia. After treatment, cryptozoospermia (concentration less than 1 million/ml) was not improved. No adverse effects are reported.

iii. Information about the patient(s) whose results are listed in Table 9 below:
smoker, less than 20 packs a day;
no comorbidities
no other treatment is taken
no vitamin supplementation at the start of treatment

TABLE 9

| PARAMETERS | 2010 WHO Standards | Before treatment | After treatment |
| --- | --- | --- | --- |
| volume | >1.5 ml | >1.5 ml | >1.5 ml |
| pH | 7.2-8 | 7.2-8 | 7.2-8 |
| Count | 15 million/ml >39 million | 10 million/ml 40 million | no change |
| Motility | >40% total motility >32% progressive motility | 27% total motility | 32% total motility |
| Morphology | >4% according to Kruger | 1% | 4% |
| Vitality | >58% | 52% | 55% |
| leukocytes | <1 million/ml | <1 million/ml | <1 million/ml |

Conclusion on the results presented in Table 9:

Before treatment, the patient has a normal-low sperm count of 40 million sperm per ejaculate. Sperm concentration is low, at 10 million/ml. Sperm motility is also low, at 27%. Vitality is about 52% and the morphology is abnormal to 1% of typical forms.

After treatment, there is:
a 32% improvement in the motility and 55% in vitality; and
an improvement of 4% in morphology of normal forms.

On the other hand, the count and concentration remain unchanged. No adverse effects are reported.

iv. Information about the patient(s) whose results are listed in Table 10 below:
Between 20-50 years
Healthy subjects with a balanced diet
Exclusion of azoospermia and excretory sterility
non-smoker
grade 1 left varicocele (Varicocele is characterised by the dilation of a vein (varicose vein) in the spermatic cord, a fibrous cord located in the sacs above each testicle, which connects each one to the scrotum)
no comorbidities
no other treatment is taken
no vitamin supplementation at the start of treatment

TABLE 10

| PARAMETERS | 2010 WHO Standards | Before treatment | After treatment |
| --- | --- | --- | --- |
| volume | >1.5 ml | 1.8 ml | 2.5 ml |
| pH | 7.2-8 | 7.2-8 | 8.1 |
| Count | 15 million/ml >39 million | 1000/ml 15M | 0.6M/ml |
| Motility | >40% total motility >32% progressive motility | 7% progressive | 46% total 28% progressive |
| leukocytes | <1 million/ml | — | 2% |

In addition, the patient evaluated the product as shown in Table 11 below:

TABLE 11

| Patient satisfaction questionnaire: | | |
| --- | --- | --- |
| How do you judge the effectiveness of this product on the improvement of spermogram parameters? | 0 = Very effective 1 = Quite effective 2 = Not very effective 3 = Completely ineffective | x |
| How do you judge the acceptability of this product (in terms of intake constraints, possible taste of the tablets, etc)? | 0 = Very good 1 = Good 2 = Average 3 = Bad | x |
| Would you agree to use this product on a regular basis? | 1 = Yes, definitely 2 = Yes, if necessary 3 = Not at all | x |

Conclusion on the results presented in Table 10:

Before treatment, the patient has a low sperm concentration at 1000/ml. Sperm motility is also low, at 7%.

After treatment, there is:
- an increase in volume;
- a significant increase in sperm concentration to 0.6M/ml
- a large improvement in motility to 46% total and 28% progressive.

Patients consider the treatment to be quite effective. No adverse effects are reported.

v. Information about the patient(s) whose results are listed in Table 12 below:
- non-smoker
- Between 20-50 years
- Healthy subjects with a balanced diet
- Exclusion of azoospermia and excretory sterility
- no other treatment is taken
- no comorbidities
- no vitamin supplementation at the start of treatment

TABLE 12

| PARAMETERS | 2010 WHO Standards | Before treatment | After treatment |
| --- | --- | --- | --- |
| volume | >1.5 ml | 4 ml | 3 ml |
| pH | 7.2-8 | 7.8 | 7.8 |
| Count | 15 million/ml >39 million | 17M/ml | 40M/ml |
| Motility | >40% total motility >32% progressive motility | 50% total 41% progressive | 50% total 41% progressive |
| Morphology | >4% according to Kruger | 2% | 1% |
| Vitality | >58% | 75% | 79% |
| leukocytes | <1 million/ml | 1% | 2% |

In addition, the patient evaluated the product as shown in Table 13 below:

TABLE 13

| Patient satisfaction questionnaire: | | |
| --- | --- | --- |
| How do you judge the effectiveness of this product on the improvement of spermogram parameters? | 0 = Very effective 1 = Quite effective 2 = Not very effective 3 = Completely ineffective | x |
| How do you judge the acceptability of this product (in terms of intake constraints, possible taste of the tablets, etc)? | 0 = Very good 1 = Good 2 = Average 3 = Bad | x |
| Would you agree to use this product on a regular basis? | 1 = Yes, definitely 2 = Yes, if necessary 3 = Not at all | x |

Conclusion on the results presented in Table 12:

Prior to treatment, the patient has a low sperm concentration at 15M/ml.

After treatment, there is:
- a significant increase in sperm concentration to 40M/ml
- a slight improvement in vitality to 79% is also observed.

No adverse effects are reported.

The invention claimed is:

1. A method of treatment of infertility in men with oligospermia, cryptozoospermia, azoospermia, asthenospermia, oligoasthenospermia and/or teratospermia, the method comprising:
providing an oral composition comprising a pollen extract and a pistil extract, said pollen and pistil being obtained from plants belonging to the Pinaceae and/or Poaceae family under aqueous extraction at a temperature between 30° C. and 45° C., wherein the pollen extract comprises protein pollen allergen Lol p4 from *Dactylis*

*glomerata* L. and the pollen extract and the pistil extract comprise beta-1,3-glucanase from *Zea mays* L.;

administering a daily dose to a man with oligospermia, cryptozoospermia, azoospermia, asthenospermia, oligoasthenospermia and/or teratospermia.

2. The method of claim 1, wherein the oral composition is in the form of a tablet, capsule, soft gel, semi-solid, solid, liquid, or powder.

3. The method of claim 1, wherein the composition is in capsule form and has a weight of 650 mg.

4. The method of claim 1, wherein the daily dose is administered for a period of at least three months.

5. The method of claim 1, wherein the infertility is not associated with inflammation of a microbacterial origin.

6. The method of claim 1, wherein said pollen and pistil are obtained from plants belonging to the species *Secale cereale* L., *Zea mays* L., *Pinus sylvestris* L., *Dactylis glomerata* L., or mixtures thereof.

7. The method of claim 6, wherein the composition comprises:

an aqueous pollen extract from *Secale cereale* L.;
an aqueous pollen extract from *Zea mays* L.;
an aqueous pollen extract from *Pinus sylvestris* L.;
an aqueous pollen extract from *Dactylis glomerata* L.; and
an aqueous pistil extract from *Zea mays* L.

8. The method of claim 3, wherein the capsule comprises a pollen and pistil extract from *Dactylis glomerata* L., *Secale cereale* L., and *Zea mays* L. and a pollen extract from pollens comprising *Zea mays* L., *Secale cereale* L., and *Pinus sylvestris* L.

9. The method of claim 1, wherein the oral composition comprises at least one amino acid, a carotenoid, a trace element, a vitamin and/or a root extract, taken alone or as a mixture.

10. The method of claim 9, wherein:

the amino acid is lysine, methionine, or carnitine;
the carotenoid is lycopene;
the trace element comprises zinc and/or selenium;
the vitamin is selected from one or more of vitamin B6, vitamin B9, vitamin B12, vitamin C, vitamin D and vitamin E; and
the root extract is a maca root extract (*Lepidium meyenii*).

11. The method of claim 10, wherein the trace element is zinc.

* * * * *